United States Patent
Marsh et al.

(10) Patent No.: US 11,723,763 B2
(45) Date of Patent: Aug. 15, 2023

(54) ARTICLE OF MANUFACTURE INCLUDING OCCLUSION RING HAVING INNER/OUTER REGIONS WITH ORTHOGONAL POLARIZATIONS

(71) Applicant: Innovega Inc., Bellevue, WA (US)

(72) Inventors: Jay Marsh, Bellevue, WA (US); Jerome Legerton, Bellevue, WA (US)

(73) Assignee: INNOVEGA INC., Bellevue, WA (US)

( * ) Notice: Subject to any disclaimer, the term of this patent is extended or adjusted under 35 U.S.C. 154(b) by 210 days.

(21) Appl. No.: 16/882,302

(22) Filed: May 22, 2020

(65) Prior Publication Data

US 2021/0361413 A1    Nov. 25, 2021

(51) Int. Cl.
| | |
|---|---|
| *A61F 2/16* | (2006.01) |
| *G02B 5/30* | (2006.01) |
| *G02C 7/04* | (2006.01) |
| *G02C 7/10* | (2006.01) |
| *G02C 7/12* | (2006.01) |
| G02C 7/16 | (2006.01) |

(52) U.S. Cl.
CPC .......... *A61F 2/1618* (2013.01); *A61F 2/1662* (2013.01); *G02B 5/3058* (2013.01); *G02C 7/041* (2013.01); *G02C 7/10* (2013.01); *G02C 7/12* (2013.01); *A61F 2230/0065* (2013.01); *A61F 2240/001* (2013.01); *A61F 2250/006* (2013.01); *G02C 7/16* (2013.01)

(58) Field of Classification Search
CPC ................ A61F 2/1618; A61F 2/1662; A61F 2230/0065; A61F 2240/001; A61F 2250/006; G02B 5/3058; G02C 7/041; G02C 7/10; G02C 7/12; G02C 7/16
See application file for complete search history.

(56) References Cited

U.S. PATENT DOCUMENTS

| | | | |
|---|---|---|---|
| 4,898,461 | A | 2/1990 | Portney |
| 7,848,003 | B2 * | 12/2010 | Kothari ................ G02B 26/001 |
| | | | 359/290 |
| 9,254,789 | B2 * | 2/2016 | Anderson ............ G02B 5/0816 |
| 9,568,677 | B2 * | 2/2017 | Tseng ..................... G02B 6/136 |
| 10,126,475 | B2 * | 11/2018 | Hasegawa ............ H05B 33/145 |

(Continued)

OTHER PUBLICATIONS

Patent Cooperation Treaty, International Searching Authority, Search Report and Written Opinion for PCT/US2021/025435, 10 pages, dated Aug. 17, 2021.

*Primary Examiner* — Ryan S Dunning
(74) *Attorney, Agent, or Firm* — Viksnins Harris Padys Malen LLP

(57) ABSTRACT

An optical article of manufacture and a method of making the article of manufacture are disclosed. The article of manufacture includes an optical component including a junction between a first region having a first optical power and a second region having a second optical power. The first optical power is different from the second optical power. The article further includes an occlusion ring included in the optical component and aligned with the junction. The method includes forming a thin film polymer layer on a substrate. The method further includes forming an occlusion ring on the thin film polymer layer. The occlusion ring has an inner occlusion ring region and an outer occlusion ring region. The method further includes forming an outer wire grid polarizer on the outer occlusion ring region.

8 Claims, 8 Drawing Sheets

(56) References Cited

U.S. PATENT DOCUMENTS

| | | |
|---|---|---|
| 2008/0002147 A1 | 1/2008 | Haywood et al. |
| 2010/0103371 A1 | 4/2010 | Sarver et al. |
| 2011/0029073 A1 | 2/2011 | Liang |
| 2013/0135723 A1* | 5/2013 | Kwon .................... G02B 30/25 29/458 |
| 2013/0182215 A1 | 7/2013 | Tung |
| 2017/0248796 A1* | 8/2017 | Banks .................. H04N 13/271 |
| 2019/0377198 A1* | 12/2019 | Lemoff .................. G02C 11/10 |

* cited by examiner

ARTICLE OF MANUFACTURE INCLUDING OCCLUSION RING HAVING INNER/OUTER REGIONS WITH ORTHOGONAL POLARIZATIONS

BACKGROUND

The present disclosure relates to articles of manufacture for use in optical systems and methods of manufacture for making those articles, and particularly to structures and methods to improve the performance of optical systems. An optical system can include structures that scatter light in a way that forms undesired artifacts, such as halos, in mages formed by the optical system. Aspects of the disclosed embodiments address this and other concerns regarding optical systems.

SUMMARY

Consistent with the disclosed embodiments, an article of manufacture comprises an optical component including a junction between a first region having a first optical power and a second region having a second optical power is disclosed. The first optical power is different from the second optical power. The article of manufacture further comprises an occlusion ring included in the optical component and aligned with the junction. In some embodiments, the optical component is included in an intraocular lens. In some embodiments, the optical component is included in a non-intraocular contact lens. In some embodiments the first and second optical power is in the finished lens such that the article of manufacture comprises an occlusion ring that will be aligned with the junction of the junction of the first and second optical power in the finished lens. The article of manufacture is comprised of at least one filter in the inner occlusion ring region or the outer inclusion ring region Consistent with the disclosed embodiments, an article of manufacture comprising an occlusion ring and an inner filter is disclosed. The occlusion ring is formed on a thin film polymer layer. The occlusion ring has an inner occlusion ring region and an outer occlusion ring region. The inner filter is formed on the thin film polymer layer in the inner occlusion ring region. In some embodiments, the inner filter comprises a spectral filter. In some embodiments, the article of manufacture further comprises an outer wire grid polarizer formed on the thin film polymer layer in the outer occlusion ring region. In some embodiments, the inner filter comprises an inner wire grid polarizer having an inner wire grid polarization and the outer wire grid polarizer has an outer wire grid polarization substantially orthogonal to the inner wire grid polarization.

Consistent with the disclosed embodiments, a method of forming an optical structure or component is disclosed. The method comprises forming a thin film polymer layer on a substrate. The method further comprises forming an occlusion ring on the thin film polymer layer. The occlusion ring has an inner occlusion ring region and an outer occlusion ring region. The method further comprises forming an outer wire grid polarizer on the outer occlusion ring region. The outer wire grid polarizer has a first polarization. In some embodiments forming an occlusion ring on the thin film polymer layer further comprises forming a thin film metal layer on the thin film polymer layer. The method further comprises processing the thin film metal layer to form the occlusion ring. In some embodiments, the method further comprises forming an inner wire grid polarizer on the inner occlusion ring region. The inner wire grid polarizer has a second polarization, the second polarization substantially orthogonal to the first polarization.

Consistent with the disclosed embodiments, an article of manufacture is disclosed. The article of manufacture comprises a substrate. The article of manufacture further comprises a thin film polymer layer formed on the substrate. The article of manufacture further comprises an array formed on the thin film polymer layer. The array includes one or more optical structures. Each of the one or more optical structures includes an occlusion ring formed on the thin film polymer. The occlusion ring has an inner polymer region and an outer polymer region. Each of the one or more optical structures further includes an inner wire grid polarizer formed on the inner polymer region. The inner wire grid polarizer has a first polarization. Each of the one or more optical structures includes an outer wire grid polarizer formed on the outer polymer region. The outer wire grid polarizer has a second polarization. The second polarization is substantially orthogonal to the first polarization.

Consistent with the disclosed embodiments, a method is disclosed. The method comprises forming a plurality of components on a polyimide sheet on a substrate. The method further comprises forming and trimming the polyimide sheet to form a plurality of meniscus shaped components. In some embodiments, forming the plurality of components on the polyimide sheet on the substrate comprises forming at least one of the plurality of components to include a first wire grid polarizer separated from a second wire grid polarizer by an occlusion ring. In some embodiments, the method further comprises combining one of the plurality of meniscus shaped components with a liquid polymer to form a lens. In some embodiments, combining one of the plurality of meniscus shaped components with the liquid polymer to form the lens includes transferring the wire grid polarizer and the occlusion ring from the polyimide to the lens. In some embodiments, combining one of the plurality of meniscus shaped components with the liquid polymer to form the lens includes transferring the wire grid polarizer and the occlusion ring from the polyimide and placing a preformed microlens in the inner occlusion ring region of the article before transferring the article to the lens. The microlens has a higher index of refraction than the lens and comprises the second optical power that is greater than the first optical power in the outer occlusion ring region and the edge of the microlens forms the junction that is aligned with the occlusion ring.

Consistent with the disclosed embodiments, a method is disclosed. The method comprises forming a plurality of components on a polyimide sheet on a substrate. The method further comprises trimming the polyimide sheet to form a plurality of flat components. In some embodiments, forming the plurality of components on the polyimide sheet on the substrate comprises forming at least one of the plurality of components to include a first wire grid polarizer separated from a second wire grid polarizer by an occlusion ring. In some embodiments, the method further comprises combining one of the plurality of flat components with a liquid polymer to form an intraocular lens. In some embodiments, the method further comprises surgically implanting one of the plurality of flat components into a preformed intraocular lens. The intraocular lens may be in a pre-surgical state or may be in the eye.

DESCRIPTION

Reference will now be made in detail to the embodiments implemented according to this disclosure, the examples of which are illustrated in the accompanying drawings.

Figure 1:
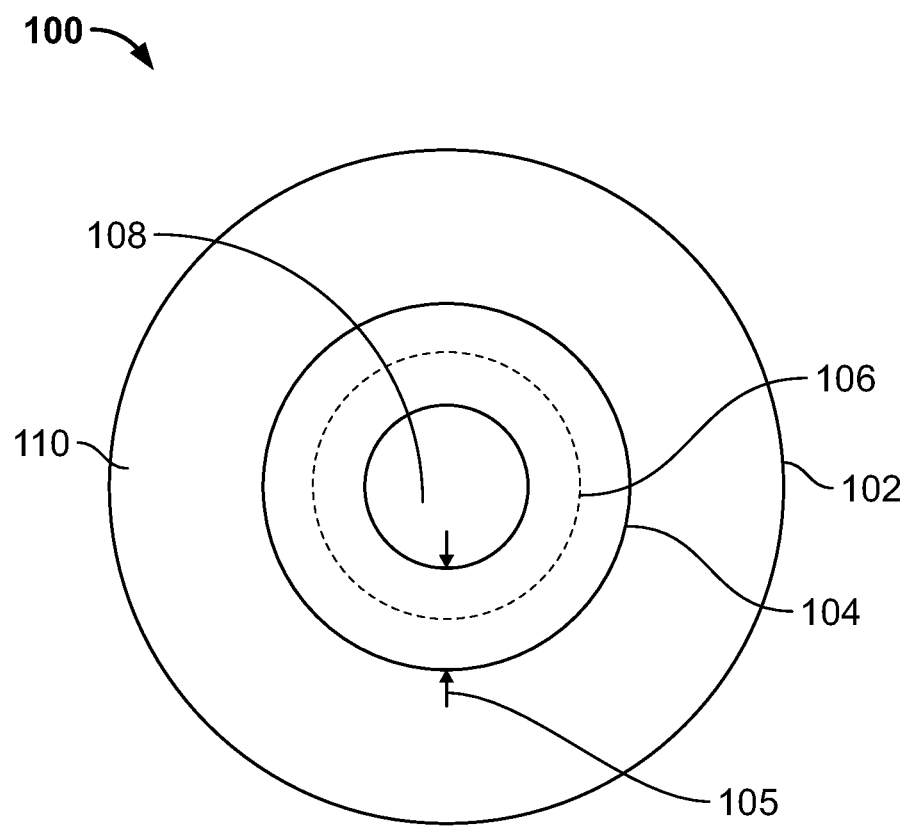
FIG. 1 shows an illustration of an article of manufacture including an optical component and an occlusion ring in accordance with some embodiments of the present disclosure.

FIG. 1 shows an illustration of an article of manufacture 100 including an optical component 102 and an occlusion ring 104 in accordance with some embodiments of the present disclosure. The optical component 102 includes a junction 106 between a first region 108 having a first optical power and a second region 110 having a second optical power. The first optical power is different from the second optical power. The occlusion ring 104 is included in the optical component 102 and aligned with the junction 106. The optical component 102 is not limited to being formed from a particular material. In some embodiments, the optical component includes a polymer.

The inclusion ring 104 is formed to prevent light from being scattered by the junction 106. The occlusion ring 104 is not limited to being formed from a particular material. In some embodiments, the occlusion ring 104 includes a metal, such as aluminum. An exemplary method for forming the occlusion ring 104 includes depositing aluminum on the junction 106 of the optical component 102 and processing the aluminum to form the occlusion ring 104 using photolithographic methods. The occlusion ring 104 has an occlusion ring width 105. The occlusion ring width 105 is not limited to a particular value. In some embodiments, the occlusion ring width 105 is between about 0.1 millimeters and about 1.0 millimeters. In some embodiments, the occlusion ring width 105 is about 0.125 millimeters. The occlusion ring 104 is ineffective to extend depth of focus of the optical component 102. The occlusion ring 104 is also not effective to function as an optical stop of the optical component 102. Hence, the occlusion ring 104 cannot serve as an aperture of the optical component 102.

In operation, the occlusion ring 104 of the optical component 102 blocks light directed to the junction 106 to prevent the light from being scattered by the junction 106. Thus, the occlusion ring 104 blocks an optical defect when two optical surfaces intersect. The junction 106 is the region of the optical component 102 where the first region 108 meets the second region 110. The occlusion ring 104 unexpectedly substantially removes undesired optical effects in images formed by the optical component 102 that includes the junction 106. For example, when the occlusion ring 104 includes a linear polarizer in the first region 108 and no filter in the second region 110, the occlusion ring 104 substantially prevents optical defects from being formed by light sources imaged by the optical component 102.

As used herein, the term contact lens includes an intraocular lens that is surgically implanted as well as a contact lens applied to the external ocular surface. In some embodiments, the optical component 102 is included in a non-intraocular contact lens. In some embodiments, the optical component 102 is included in an intraocular contact lens.

Figure 2:
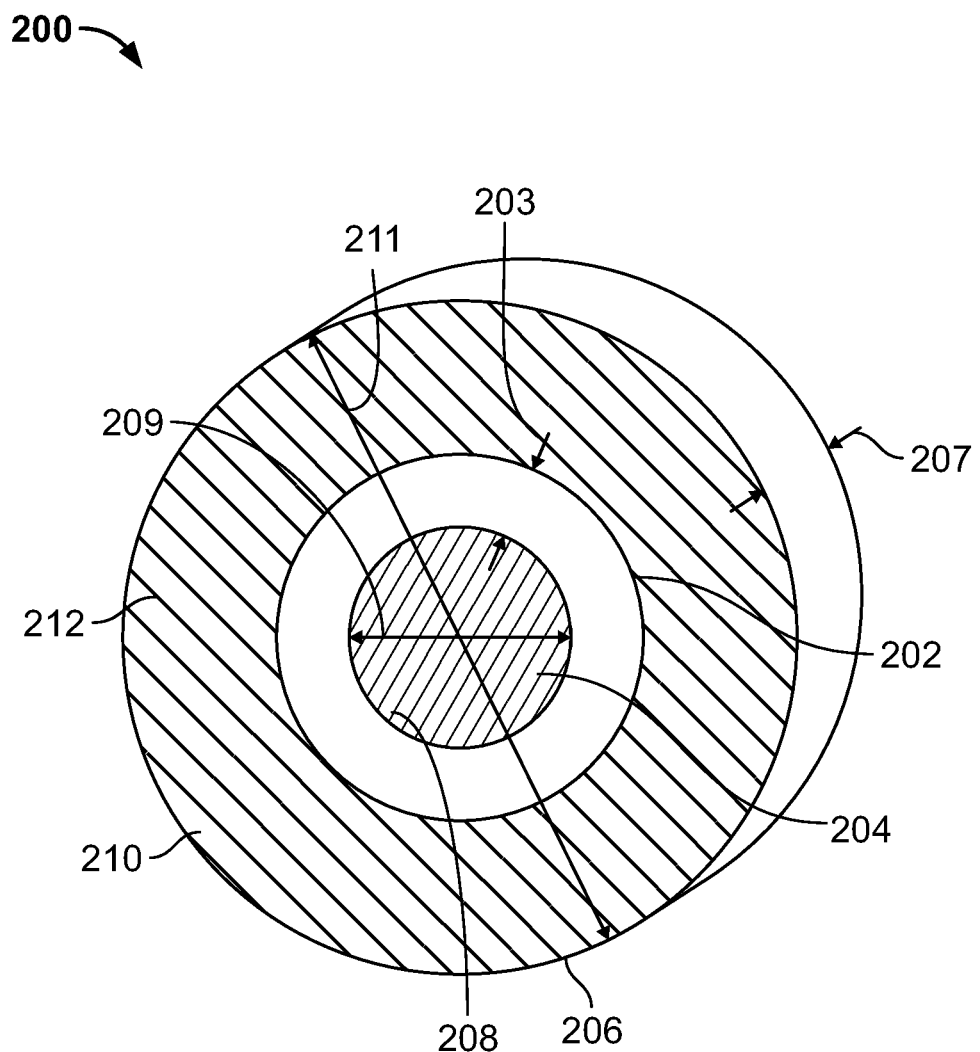
FIG. 2 shows an illustration of an article of manufacture that includes an occlusion ring and an inner filter in accordance with some embodiments of the present disclosure.

FIG. 2 shows an illustration of an article of manufacture 200 that includes an occlusion ring 202 and an inner filter 204 in accordance with some embodiments of the present disclosure. The occlusion ring 202 is formed on a thin film polymer layer 206. The occlusion ring 202 has an inner occlusion ring region 208 and an outer occlusion ring region 210. The inner filter 204 is formed on the thin film polymer layer 206 in the inner occlusion ring region 208. In some embodiments, the article of manufacture 200 is suitable for use in a process for manufacturing a contact lens that includes the occlusion ring 202 and the inner filter 204. In some embodiments, the occlusion ring 202 and the inner filter 204 are separated from the thin film polymer layer 206 and included in the manufacturing process for a contact lens.

The thin film polymer layer 206 is not limited to a particular material. Exemplary materials suitable for use in the fabrication of the thin film polymer layer 206 have a water solubility less than about one percent. Exemplary materials suitable for use in the fabrication of the thin film polymer layer 206 have a glass transition temperature greater than about 190 degrees centigrade and less than the material's decomposition temperature. The thin film polymer layer 206 may be hydrophobic or hydrophilic. In some embodiments, the thin film polymer layer 206 is formed from a thermoplastic, such as a polyimide. A polyimide is a polymer of imide monomers. In some embodiments, the thin film polymer layer 206 is formed from a polysulfone. The thin film polymer layer 206 has a thin film polymer layer thickness 207. In some embodiments, the thin film polymer layer thickness 207 is between about 1 micron and about 80 microns. In some embodiments, the thin film polymer layer thickness 207 is between about 5 microns and 25 microns.

The thin film polymer layer 206 can be formed to have shaped surfaces. In some embodiments, the thin film polymer layer 206 is formed to have an anterior surface that is convex. In some embodiments, the thin film polymer layer 206 is formed to have a substantially uncurved surface. A substantially uncurved surface is a surface that does not substantially vary from being flat. In some embodiments, the thin film polymer layer 206 is shaped to have a posterior surface that is substantially concave. In some embodiments, the thin film polymer layer 206 is shaped to have a posterior surface that is substantially uncurved.

The occlusion ring 202 is not limited to being formed from a particular material. In some embodiments, the occlusion ring 202 includes a metal, such as aluminum. An exemplary method for forming the occlusion ring 202 includes depositing aluminum on the thin film polymer layer 206 and processing the aluminum to form the occlusion ring 202 using photolithographic methods. The occlusion ring 202 has an occlusion ring width 203. The occlusion ring width 203 is not limited to a particular value. In some embodiments, the occlusion ring width 203 is between about 0.1 millimeters and about 1.0 millimeters. In some embodiments, the occlusion ring width 203 is about 0.125 millimeters.

The inner occlusion ring region 208 has an inner occlusion ring region diameter 209. The inner occlusion ring region diameter 209 is not limited to a particular value. In some embodiments, the inner occlusion ring region diameter 209 is between about 0.7 millimeters and 1.5 millimeters. In some embodiments, the inner occlusion ring region diameter 209 is about 1.0 millimeters.

The outer occlusion ring region 210 has an outer occlusion ring region diameter 211. The outer occlusion ring region diameter 211 is not limited to a particular value. In some embodiments, the outer occlusion ring region diameter 211 is between about 5.0 millimeters and about 13 millimeters. In some embodiments, the outer occlusion ring region diameter 211 is about 5.0 millimeters. In some embodiments, the outer occlusion ring region diameter 211 is about 8.5 millimeters.

The inner filter 204 is not limited to a particular type of filter. In some embodiments, the inner filter 204 includes a light polarizing filter. In some embodiments, the inner filter 204 includes a spectral filter. Exemplary spectral filters suitable for use in connection with the fabrication of the article of manufacture 200 include three band, bandpass filters. In some embodiments, the inner filter 204 includes a broad spectrum filter. Exemplary broad spectrum filters suitable for use in the fabrication of the article of manufacture 200 include photochromic filters, electrochromic filters, and neutral density filters.

In some embodiments, the outer occlusion ring region 210 includes an outer light polarizing filter. In some embodiments, the outer filter includes a spectral filter. Exemplary spectral filters suitable for use in connection with the fabrication of the outer filter of the article of manufacture 200 include three band, notch filters. In some embodiments, the outer filter includes a broad spectrum filter. Exemplary broad spectrum filters suitable for use in the fabrication of the article of manufacture 200 include photochromic filters, electrochromic filters, and neutral density filters.

In some embodiments, the article of manufacture 200 further includes an outer wire grid polarizer 212 formed on the thin film polymer layer 206 in the outer occlusion ring region 210. In some embodiments, the inner filter 204 includes an inner wire grid polarizer 214 having an inner wire grid polarization and the outer wire grid polarizer 212 having an outer wire grid polarization. The outer wire grid polarization is substantially orthogonal to the inner wire grid polarization. In some embodiments, the inner wire grid polarizer 204 includes an array of thin metal structures formed on the thin film polymer layer 206. In some embodiments, the outer wire grid polarizer 212 includes an ordered arrangement of thin metal structures formed on the thin film polymer layer 206. In some embodiments, the inner polarizer 204 and the outer polarizer 212 are reflective polarizers and only pass light oscillating perpendicular to their structures. The inner polarizer 204 and the outer polarizer 212 are not limited to particular types of polarizers. In some embodiments, the inner polarizer 204 includes an absorptive polarizer. In some embodiments, the outer polarizer 212 includes an absorptive polarizer.

In some embodiments, in operation the occlusion ring 202 and the inner filter 204 of the article of manufacture 200 are included in a contact lens including a non-intraocular contact lens or intraocular contact lens. The outer filter wire grid polarizer 204 is transmission aligned to the transmission polarization of an associated spectacle lens and the inner wire grid polarizer transmission direction is substantially orthogonal to the transmission polarization of the spectacle lens. If a micro-display is included in an embodiment, then the polarization of the light from the micro-display is substantially orthogonal to the transmission polarization of the outer wire grid polarizer 212.

Figure 3:
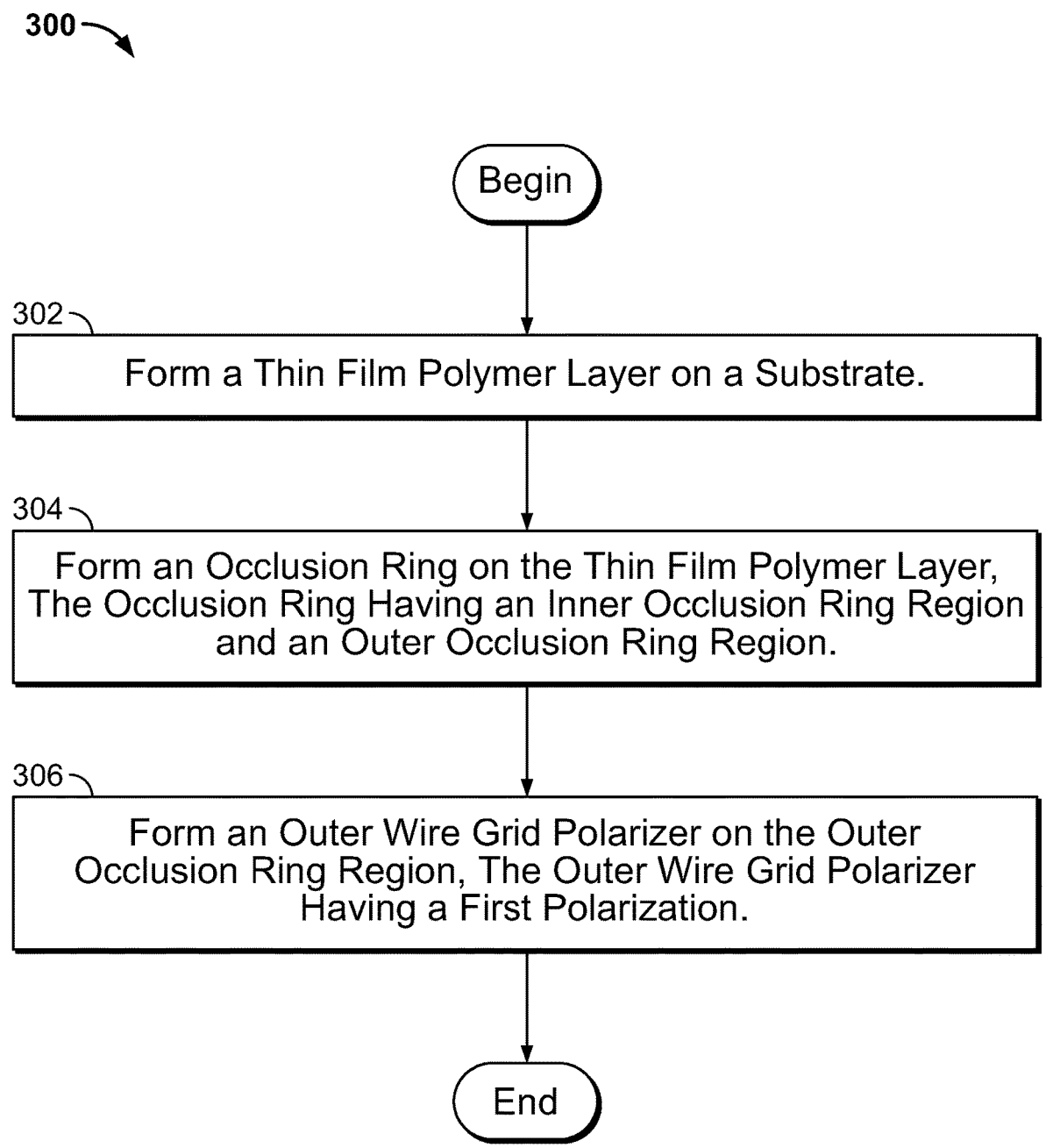
FIG. 3 shows a flow diagram of a method for forming an optical article of manufacture in accordance with some embodiments of the present disclosure.

FIG. 3 shows a flow diagram of a method 300 for forming an optical article of manufacture in accordance with some embodiments of the present disclosure. The method 300 includes forming a thin film polymer layer on a substrate (block 302), forming an occlusion ring on the thin film polymer layer, the occlusion ring having an inner occlusion ring region and an outer occlusion ring region (block 304), and forming an outer wire grid polarizer on the outer occlusion ring region, the outer wire grid polarizer having a first polarization (306).

In some embodiments, forming an occlusion ring on the thin film polymer layer includes forming a thin film metal layer on the thin film polymer layer and processing the thin film metal layer to form the occlusion ring. In some embodiments, the method 300 further includes forming an inner wire grid polarizer in the inner occlusion ring region; the inner wire grid polarizer has a second polarization, and the second polarization is substantially orthogonal to the first polarization.

Figure 4A:
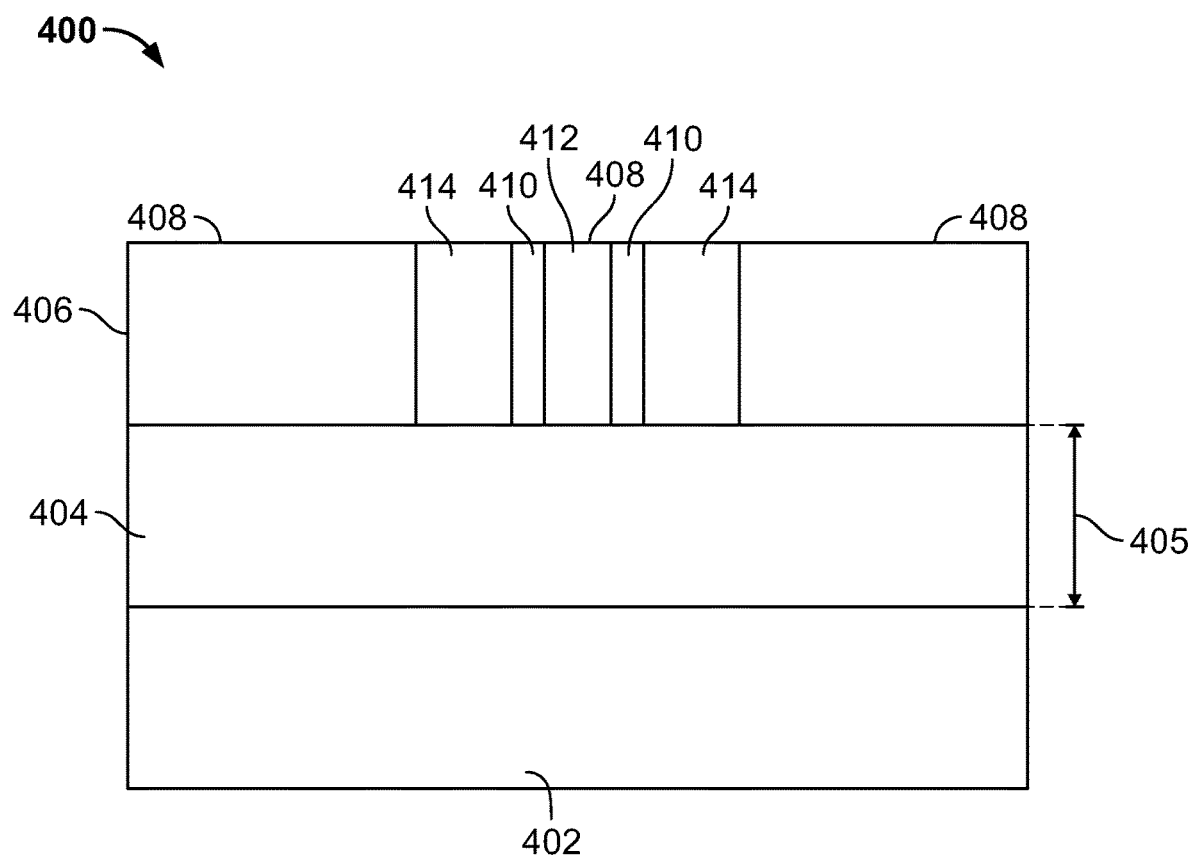
FIG. 4A shows an illustration of a cross-section side view of an article of manufacture including a substrate, a thin film polymer layer, and the one or more optical structures in accordance with some embodiments of the present disclosure.

FIG. 4A shows an illustration of a cross-section side view of an article of manufacture 400 including a substrate 402, a thin film polymer layer 404, and an ordered arrangement 406 including one or more optical structures 408 in accordance with some embodiments of the present disclosure. The substrate 402 provides a base for supporting the thin film polymer layer 404. In some embodiments, the substrate 402 includes a slice of monocrystalline silicon. The term substrate as used herein is not limited to a solid, inflexible substrate. In some embodiments, the substrate 402 is a flexible sheet, such as a polymer sheet used in roll-to-roll processing. Roll-to-roll processing includes forming electronic or optical devices on a roll of material, such as a plastic, metal, or polymer. Multiple processes may be applied to the roll of material to create complex optical or electrical devices in roll-to-roll processing. The thin film polymer layer 404 is formed on the substrate 402. Exemplary materials suitable for use in the fabrication of the thin film polymer layer 404 have a water solubility less than about one percent. Exemplary materials suitable for use in the fabrication of the thin film polymer layer 404 have a glass transition temperature greater than about 190 degrees centigrade and less than the material's decomposition temperature. The thin film polymer layer 404 may be hydrophobic or hydrophilic. Exemplary polymers, suitable for use in the fabrication of the article of manufacture 400, include polymers, such as polyimide and polysufone. The thin film polymer layer 404 has a thin film polymer layer thickness 405. In some embodiments, the thin film polymer layer thickness 405 is between about 1 micron and about 80 microns. In some embodiments, the thin film polymer layer thickness 405 is between about 5 microns and 25 microns. The ordered arrangement 406 is formed on the thin film polymer layer 404 and includes the one or more optical structures 408 including structures such as an occlusion ring 410, an inner wire grid polarizer 412, and an outer wire grid polarizer 414.

Figure 4B:
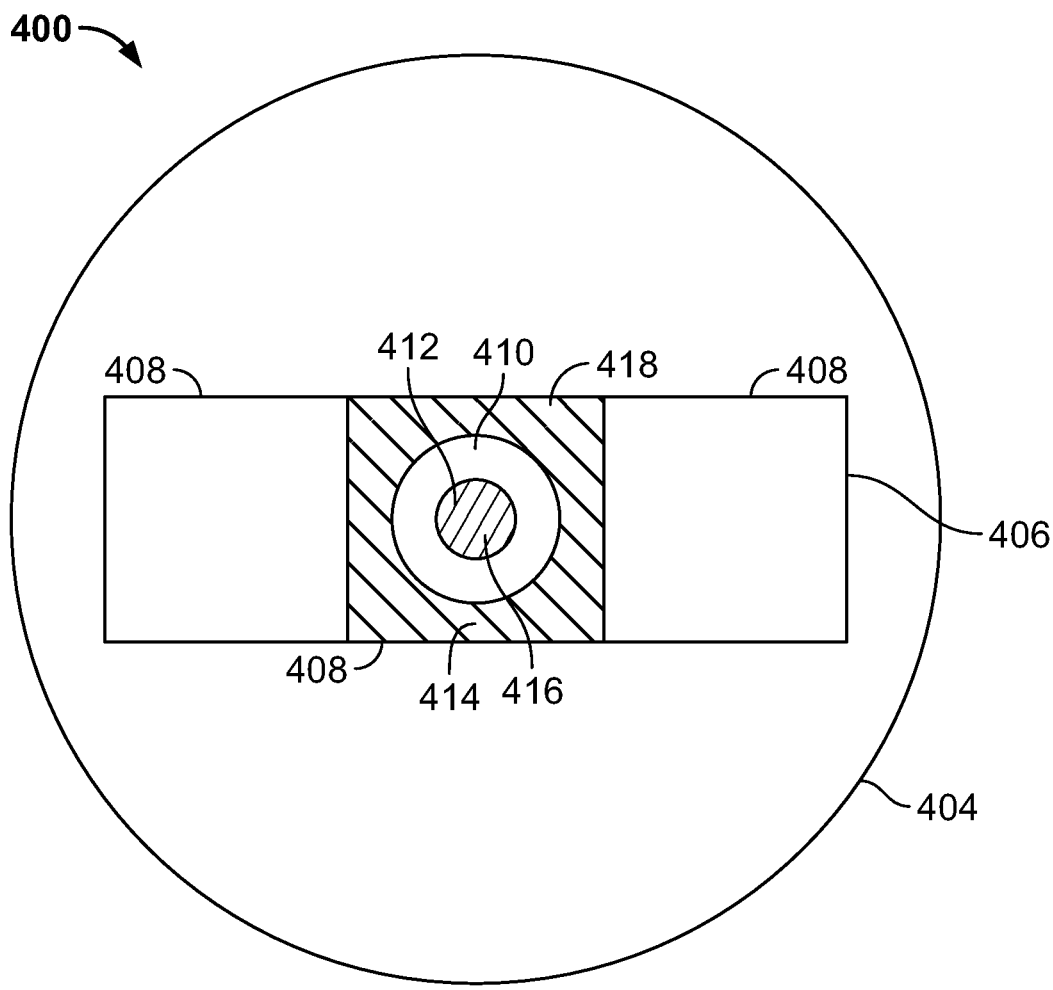
FIG. 4B shows an illustration of a top view of the article of manufacture shown in FIG. 4A including the thin film polymer layer and the one or more optical structures in accordance with some embodiments of the present disclosure.

FIG. 4B shows an illustration of a top view of the article of manufacture 400 including the thin film polymer layer 404 and the ordered arrangement 406 including the one or more optical structures 408 in accordance with some embodiments of the present disclosure. In some embodiments, each of the one or more optical structures 408 includes an occlusion ring 410, an inner wire grid polarizer 412, and an outer wire grid polarizer 414. The occlusion ring 410 is formed on the thin film polymer layer 404. The occlusion ring 410 has an inner polymer region 416 and an outer polymer region 418. The inner wire grid polarizer 412 has a first polarization and is formed on the inner polymer region 416. The outer wire grid polarizer 414 has a second polarization and is formed on the outer polymer region 418. The first polarization is substantially orthogonal to the second polarization.

Figure 5:
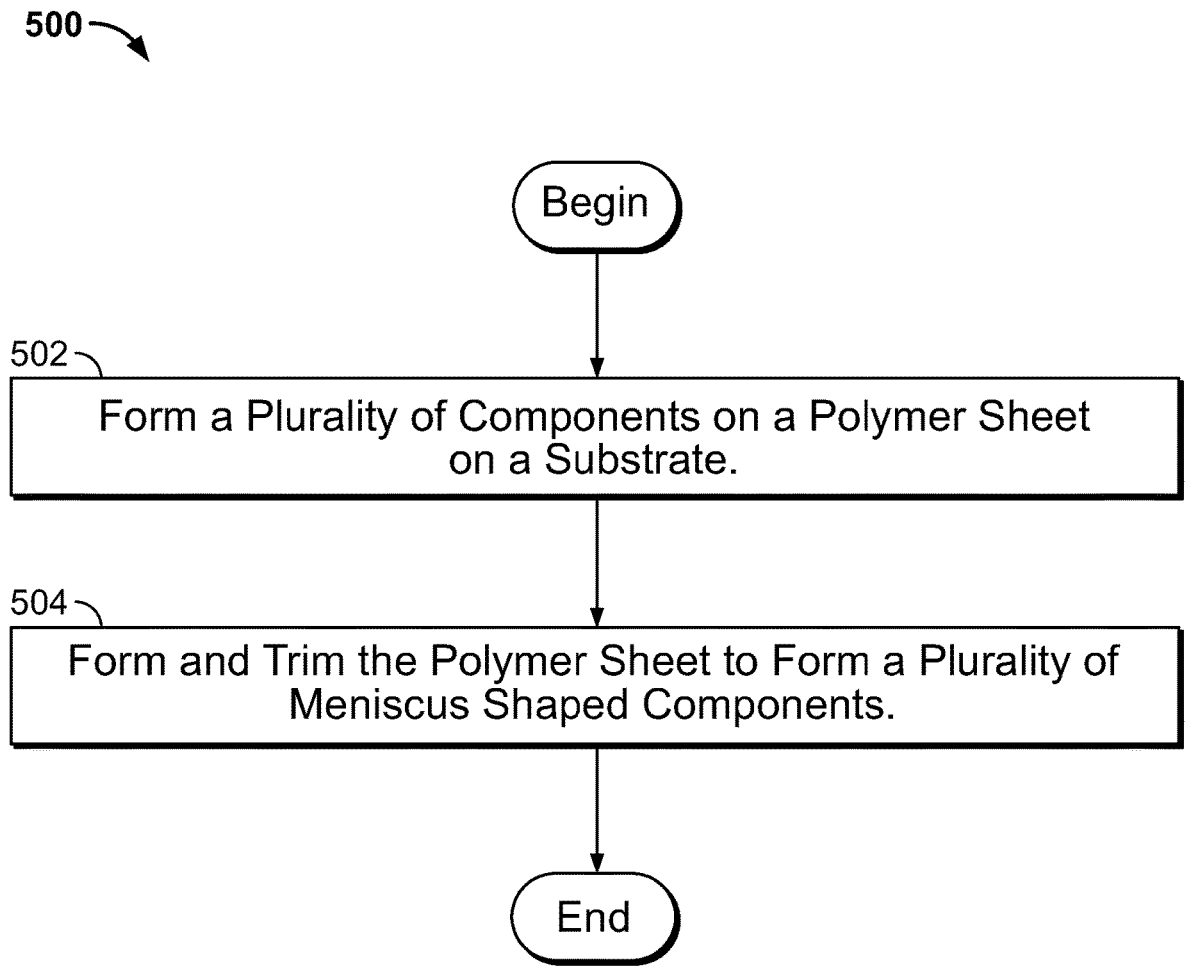
FIG. 5 shows a flow diagram of a method to form a plurality of meniscus shaped components in accordance with some embodiments of the present disclosure.

FIG. 5 shows a flow diagram of a method 500 to form a plurality of meniscus shaped components in accordance with some embodiments of the present disclosure. The method 500 includes forming a plurality of components on a polymer sheet on a substrate (block 502), and forming and trimming the polymer sheet to form a plurality of meniscus shaped components (block 504). Trimming includes but is not limited to laser trimming, knife trimming, scissor trimming, die-cutting, scribe trimming, or chemical trimming including masking and etching. "Forming and trimming" is not limited to a particular forming process. Forming includes thermoforming, room temperature mechanical forming, room temperature pressurized forming, and chemical weakening followed by mechanical or pressurized stretching. As used herein, the term "pressurized" includes vacuum processes in which a pressure differential across the film performs the forming.

In some embodiments, forming the plurality of components on the polymer sheet on the substrate includes forming at least one of the plurality of components to include a first wire grid polarizer separated from a second wire grid polarizer by an occlusion ring.

In some embodiments, the method 500 further includes combining one of the plurality of meniscus shaped components with a liquid polymer to form a lens.

In some embodiments, wherein combining one of the plurality of meniscus shaped components with the liquid polymer to form the lens includes transferring the wire grid polarizer and the occlusion ring from the polyimide to the lens.

In some embodiments, the method 500 further includes combining one of the plurality of meniscus shaped components with a liquid polymer to form an article of manufacture having a second polymer layer. Materials suitable for use as the second polymer layer include hydrogel, silicone hydrogel and silicone elastomer contact lens materials as well as hydrophilic and hydrophobic intraocular lens materials.

In some embodiments, wherein combining one of the plurality of meniscus shaped components with the liquid polymer to form an article of manufacture having a second polymer layer includes transferring the wire grid polarizer and the occlusion ring from the polyimide to the cured second polymer layer and removing the polyimide layer.

In some embodiments, wherein combining one of the plurality of meniscus shaped components with the liquid polymer to form an article of manufacture having a second polymer layer and having the wire grid polarizer and the occlusion ring transferred to the cured second polymer layer and having the polyimide removed includes combining the article of manufacture with a liquid polymer to form a lens.

Figure 6:
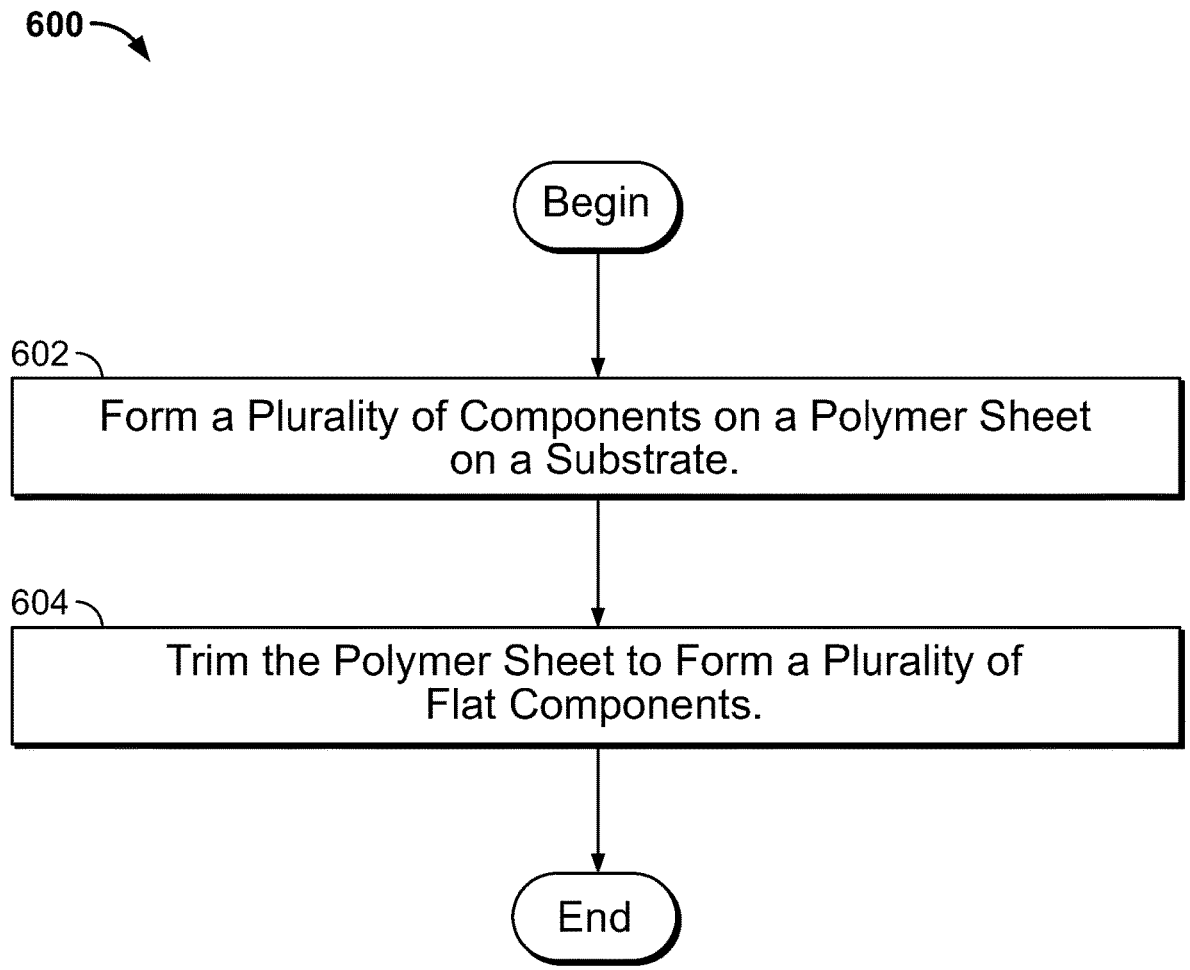
FIG. 6 shows a flow diagram of a method for forming a plurality of flat components in accordance with some embodiments of the present disclosure.

FIG. 6 shows a flow diagram 600 of a method for forming a plurality of flat components in accordance with some embodiments of the present disclosure. The flow diagram 600 of the method 600 includes forming a plurality of components on a polyimide sheet on a substrate (block 602), and trimming the polyimide sheet to form a plurality of flat components (block 604).

In some embodiments wherein forming the plurality of components on the polyimide sheet on the substrate includes forming at least one of the plurality of flat components to include a first wire grid polarizer separated from a second wire grid polarizer by an occlusion ring.

In some embodiments, the method 600 further includes combining one of the plurality of flat components with a liquid polymer to form an intraocular lens.

In some embodiments, the method 500 further includes combining one of the plurality of flat components with a liquid polymer to form an article of manufacture having a second polymer layer.

In some embodiments, wherein combining one of the plurality of flat components with the liquid polymer to form an article of manufacture having a second polymer layer includes transferring the wire grid polarizer and the occlusion ring from the polyimide to the cured second polymer layer and removing the polyimide layer.

In some embodiments, wherein combining one of the plurality of flat components with the liquid polymer to form an article of manufacture having a second polymer layer and having the wire grid polarizer and the occlusion ring transferred to the cured second polymer layer and having the polyimide removed includes combining the article of manufacture with a liquid polymer to form an intraocular.

In some embodiments, the method 600 further includes surgically implanting one of the plurality of flat components into a preformed intraocular lens that is already in the eye.

Figure 7:
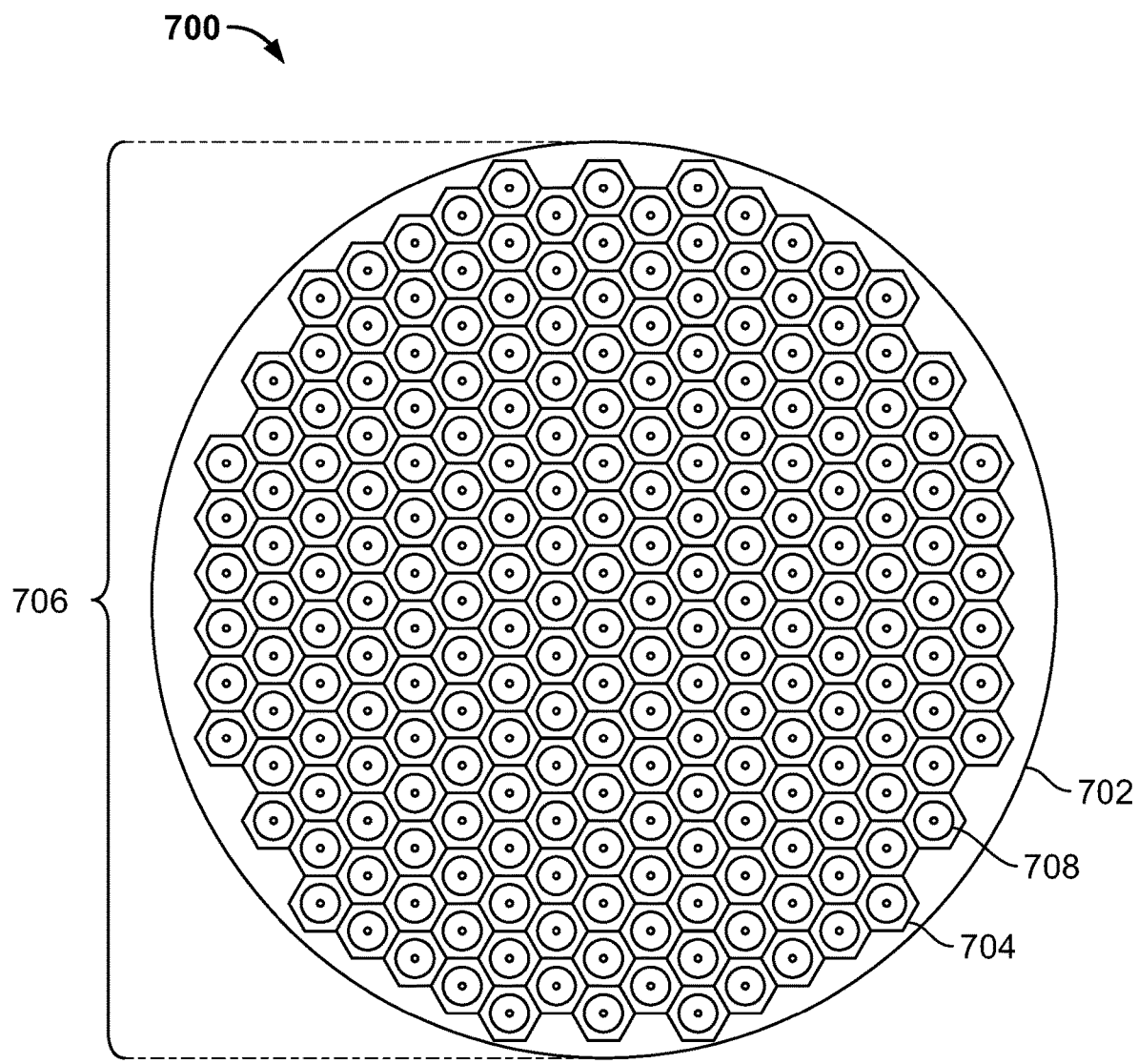
FIG. 7 shows an article of manufacture including a substrate and thin film polymer layer formed on the substrate and including an array of components in accordance with some embodiments of the present disclosure.

FIG. 7 shows an article of manufacture 700 including a substrate 702 and thin film polymer layer 704 formed on the substrate 702 and including an array 706 of components 708 in accordance with some embodiments of the present disclosure. The substrate 702 is not limited to a particular material. In some embodiments, the substrate 702 includes a crystalline silicon such as the crystalline silicon used as a substrate in the manufacture of integrated circuits. In some embodiments, the substrate 702 is formed from a flexible material, such as a flexible plastic. The thin film polymer layer 704 formed on the substrate 702 is not limited to a particular material. In some embodiments, the polymer layer 704 is a polyimide. In some embodiments, the polymer layer 704 is a polysulfone. The components 708 of the array 706 include but are not limited to electrical, optical, and electrical-optical components. In some embodiments, the components 708 are optical components or structures, such as lenses, filters, or reflectors or components of lenses, filters, or reflectors.

In the preceding specification, various example embodiments have been described with reference to the accompanying drawings. It will, however, be evident that various modifications and changes can be made thereto, and additional embodiments may be implemented based on the principles of the present disclosure. The specification and drawings are accordingly to be regarded in an illustrative rather than restrictive sense.

For example, advantageous results still could be achieved if steps of the disclosed techniques were performed in a different order or if components in the disclosed systems were combined in a different manner or replaced or supplemented by other components. Other implementations are also within the scope of the following example claims.

What is claimed is:
1. An article of manufacture comprising:
   an occlusion ring formed on a thin film polymer layer, the occlusion ring having an inner occlusion ring region and an outer occlusion ring region;

an outer filter formed on the thin film polymer layer in the outer occlusion ring region; and an inner polarizer formed on the thin film polymer layer in the inner occlusion ring region;

wherein the inner polarizer has an inner polarization and the outer filter has an outer polarization substantially orthogonal to the inner polarization;

wherein the inner occlusion ring region and the outer occlusion ring region are at a same side of the thin film polymer layer.

2. The article of manufacture of claim 1, wherein the inner occlusion ring region comprises a spectral filter.

3. The article of manufacture of claim 1, wherein the thin film polymer layer has a thickness of between about five microns and about eighty microns.

4. The article of manufacture of claim 1, wherein the thin film polymer layer is formed to have a shaped surface.

5. The article of manufacture of claim 1, wherein the occlusion ring is formed from a metal.

6. The article of manufacture of claim 1, wherein the occlusion ring has a width of between about 0.1 millimeters and 1.0 millimeters.

7. The article of manufacture of claim 1, wherein the inner occlusion ring region has an inner occlusion ring diameter of between about 0.7 millimeters and about 1.5 millimeters.

8. An article of manufacture comprising:

a substrate;

a thin film polymer layer formed on the substrate; and an array formed on the thin film polymer layer, the array including one or more optical structures, each of the one or more optical structures including:

an occlusion ring formed on the thin film polymer, the occlusion ring having an inner polymer region and an outer polymer region;

an inner wire grid polarizer formed on the inner polymer region, the inner wire grid polarizer having a first polarization; and an outer wire grid polarizer formed on the outer polymer region, the outer wire grid polarizer spaced apart from the inner wire grid polarizer, the outer wire grid polarizer having a second polarization, the second polarization substantially orthogonal to the first polarization.

* * * * *